United States Patent [19]

Lardon

[11] 4,201,479
[45] May 6, 1980

[54] DEVICE FOR MEASURING THE REFLECTION OF A PLANE, SPECULARLY REFLECTING SURFACE

[75] Inventor: Marcel A. Lardon, Maienfeld, Switzerland

[73] Assignee: Balzers Aktiengesellschaft für Hochvakuumtechnik und Dünne Schichten, Liechtenstein, Liechtenstein

[21] Appl. No.: 909,808

[22] Filed: May 26, 1978

[30] Foreign Application Priority Data

Jun. 6, 1977 [CH] Switzerland ............... 6933/77

[51] Int. Cl.² ............................................. G01N 21/48
[52] U.S. Cl. ................................................... 356/445
[58] Field of Search ............... 356/445, 446, 447, 448

[56] References Cited

U.S. PATENT DOCUMENTS

| | | | |
|---|---|---|---|
| 3,229,564 | 1/1966 | Meltzer | 356/446 |
| 3,565,568 | 2/1971 | Hock | 356/448 |

FOREIGN PATENT DOCUMENTS 1959612  6/1971  Fed. Rep. of Germany .......... 356/432

OTHER PUBLICATIONS

Melsheimer et al. "Portable Visible-Infrared Reflectometer", *Rev. Sci. Instrum.* vol. 48, No. 4 (Apr. 1977) pp. 482-483.

*Primary Examiner*—John K. Corbin
*Assistant Examiner*—R. A. Rosenberger
*Attorney, Agent, or Firm*—McGlew and Tuttle

[57] ABSTRACT

The present invention relates to a device for measuring the reflection of a plane, specularly reflecting surface, in which a measuring beam of radiation is directed onto the surface to be measured through an optical converging lens and the radiation reflected from the surface is directed through the same lens to a radiation receiver. In such a system, preferably, the optical connections between the source of radiation and the converging lens and between the lens and the radiation receiver are established by means of a fiber-optical photoconductor or a lens and mirror systems. Such a device may be employed, for example, for measuring the reflection of thin layers deposited in a vacuum evaporator.

11 Claims, 5 Drawing Figures

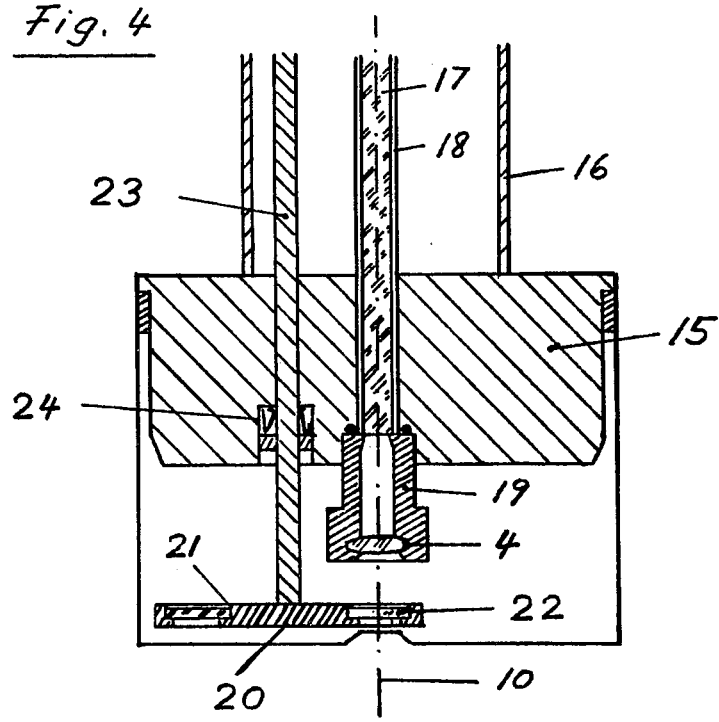
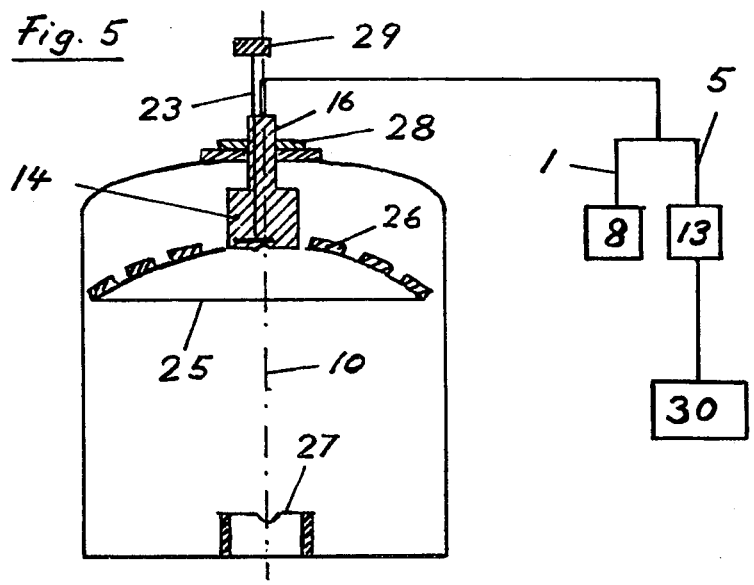

DEVICE FOR MEASURING THE REFLECTION OF A PLANE, SPECULARLY REFLECTING SURFACE

PRIOR ART

There is known a reflection measuring device for a vacuum evaporator, in which the optical fibers are collected to a bundle which is vacuum-tightly passed through the wall of the evaporation chamber, while the measuring radiation and the detector, as well as the following devices for processing the detector signal, are provided outside the vacuum chamber. The advantage of such an arrangement is that only a small space is required for the parts of the measuring device accomodated within the evaporation chamber. Like other prior art reflection measuring devices for vacuum evaporators, where the measuring beam of radiation is directed into and out of the vacuum chamber through windows, the known device operating with optical fiber conductors still has the disadvantage that the measurements do not cover a perpendicular incidence of the measuring beam of radiation on the surface to be measured. Measurements related to perpendicular incidence, however, would be desirable for the reason, among others, that at an oblique incidence, the reflective power of many measured surfaces varies with the various polarized components of the measuring radiation. In addition, the measured reflection coefficient changes even upon the slightest deviation of the angle of incidence form the assumed theoretical angle, which deviation may be due to possible inaccuracies of mounting or to a displacement of the measured surface.

The present invention is directed to a device for measuring reflections of reflecting surfaces, in which the measurement takes place under an approximately perpendicular light incidence. Also, the inventive arrangement has to ensure that the unavoidable small deviations from the perpendicularity of incidence are practically not noticeable in the results of measurement. Due to the combined effect of these two advantageous features, a result of measurement is obtained which, as far as the measuring accuracy is concerned, does correspond to a measurement with a perpendicular incidence of the measuring radiation.

For this purpose, a device of the above mentioned kind is provided in which, in accordance with the invention, the distance y of the reflecting surface and the distance x of the source of radiation or image thereof from the principal plane of the lens having a focal length f are linked to each other through the relation $$y = (2x - f / x - f) \cdot (f/2),$$

and the source of radiation is positioned in the optical axis and surrounded by a receiving surface concentrical therewith in such a manner that at the location of the receiving surface, the cross-sectional area of the reflected beam of rays falls completely within this surface and covers completely the source of radiation.

Exemplary embodiments of the invention are shown in the accompanying drawings in which FIG. 1 is a diagram showing the optical arrangement while using a fiber-optical photoconductor;

FIG. 4 shows a design by way of example of a reflection measuring head equipped with a test glass changer, for a vacuum evaporator;

FIG. 5 shows a possible arrangement of the measuring head in the evaporator.

Figure 1:
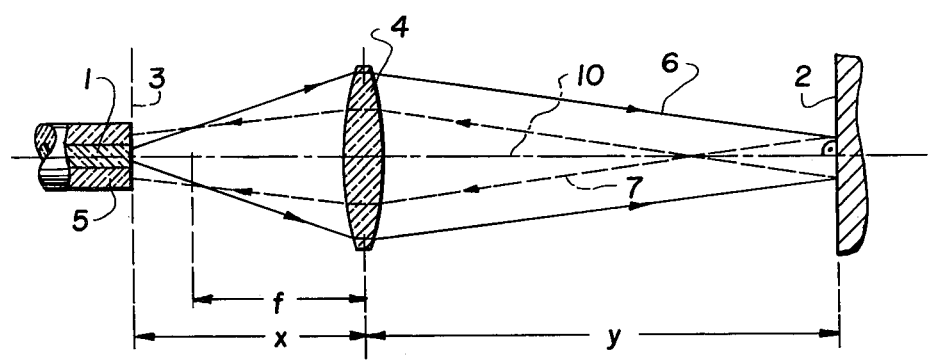
Figure 2:
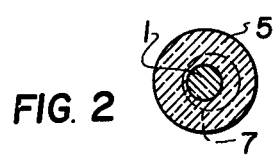
FIG. 2 shows the distribution of the fibers in the transmitting and receiving plane of the photoconductor.

In FIG. 1, the fiber bundle through which the measuring radiation is fed in is shown at 1. As the measuring radiation, an electromagnetic radiation is used having a wavelength for which the reflective power of surface 2 is to be measured, thus, for measurements in the luminous spectral region, visible light. The radiation emerges from the end face, extending in a plane 3, of the feed fiber bundle (which, therefore, acts as the source of radiation) at a definite aperture angle and is directed, through a converging lens 4, to the surface 2 to be measured where it is reflected and the reflected beam returns through the same lens to the exit fiber bundle 5 whose end face extends in the same plane 3 as the end face of the feed fiber bundle. The exit fiber bundle surrounds bundle 1 of the feed fibers concentrically (FIG. 2). FIG. 1 indicates the path of rays for a measuring beam 6 and the reflected beam 7 associated therewith. The distances x and y from the principal plane of the lens, which are determinative in accordance with this invention, and the focal length f are also indicated.

Figure 3:
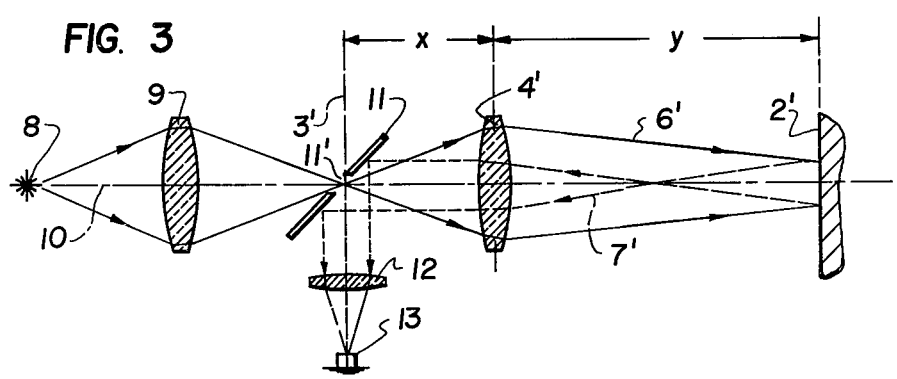
FIG. 3 is a diagram showing the optical arrangement while using a mirror and additional converging lenses.

FIG. 3 shows another embodiment of the invention. An image of a suitable source of radiation 8 (for example, a spectral lamp) is formed in a plane 3' by means of a converging lens 9. Through an aperture 11' in a mirror 11 which extends obliquely, at an angle of 45°, relative to the optical axis 10, the measuring beam of radiation 6' passes to a converging lens 4' and therethrough to the reflecting surface 2'. The reflected beam 7' returns through the same lens 4' to mirror 11 by which it is deflected to a third converging lens 12 focusing the beam on a receiver 13. It is evident that aperture 11' in mirror 11 has the same function as the end face of feed fiber bundle 1 in plane 3 of FIG. 1.

A practical, further embodiment of a measuring device in accordance with the invention is shown in FIG. 4. This device is mounted on a base plate 15 which is vacuum-tightly connected to and supported by a tube 16 which extends through the wall of the vacuum chamber to the outside (see FIG. 5). Within tube 16, the optical feed and exit fibers, which are collected to a combined bundle 17, are introduced into the device, with bundle 17 being, in addition, surrounded by a protective covering 18. Further secured to plate 15 are a mount 19 for a lens 4 (corresponding to the optical arrangement of FIG. 1) and a test glass changer. This changer comprises a turntable 20 having a plurality of openings 21 uniformly distributed over its circumference, in which test glasses 22 are to be received. Turntable 20 is actuable by means of a shaft 23 which is passed vacuum-tightly through base plate 15 to the outside and sealed by means of a lip seal 24. This makes it possible to bring the test glasses 22 sequentially into their measuring position aligned with the optical axis 10 of lens 4.

The measuring head 14 of FIG. 4 is placed in the evaporation chamber advantageously in a manner shown in FIG. 5, i.e. in the center of a support 25 of the substrates 26 to be coated. In many vacuum evaporators, support 25 is designed as a spherical cap which is mounted for rotation while being supported and driven on its circumference. Thus, the measuring head is placed in the axis of the evaporation chamber in a position which is favorable for most of the vapor deposition processes, particularly if the evaporative substance is also provided in this axis.

As shown in FIG. 5, tube 16 supporting the measuring head is secured, by means of a flange 28, to a counterflange of the evaporation chamber. Shaft 23 of the test glass changer may be actuated from outside the chamber by means of a knob 29.

FIG. 5 further indicates the connection of fiber bundles 1 and 5 to a source of radiation 8 and a radiation detector 13. The detector is connected to elements 30 for amplifying and indicating or registering the measuring signal. These parts of the device are of a kind known per se and, therefore, are not explained in detail in this specification. They may be designed in various ways, in accordance with the requirements of the measurement.

The described measuring device has the advantage that it can easily be mounted in and removed from any vacuum chamber, while providing a single flange. The displaceable and rotatable supporting tube 16 makes is possible to adjust most various measuring positions and, consequently, to adapt the measuring device to apparatus of different design. The source of radiation and the radiation receiver can be provided outside the vacuum space, at an easily accessible location, which substantially facilitates the setting. There is no need for any voluminous additional structures for these last mentioned parts of equipment within the vacuum chamber. The novel device also permits a simultaneous measurement of the reflection for radiations having different wavelengths, and in such a case the wavelengths may be separated from each other outside the vacuum chamber, by means of known optical separating filter arrangements, and supplied to detectors for determining the reflection at different wavelengths. In this way, with a sufficient number of measuring points in the spectrum, the spectral curve of a vapor-deposited layer can be followed continuously and, for example, represented on a monitor by means of a cathode-ray tube.

As optical fiber bundles for radiations within the visible and infrared region up to 1.4 microns, commercially available photoconductors are suitable. As sources of radiation, any known sources may be used, such as an incandescent lamp, but preferred are light-emitting diodes. As radiation receivers, particularly photoelectric cells and photodiodes are suitable.

While using light-emitting diodes as the source of radiation, and photodiodes as the radiation detector, the invention may easily be applied in such a way that these elements are accomodated at any location within the vacuum chamber where they do not hinder the operation, and connected to the measuring head through optical fiber conductors. In such an instance, only the electrical lines are to be passed through the wall of the vacuum chamber.

In embodied examples, the converging lens 4 had a focal length of 10 to 25 mm. The fiber bundle feeding the measuring radiation had a diameter of about 1 mm and was concentrically surrounded by the exit fiber bundle.

The cross section of the fibers of the latter was about the double of the cross section of the central fiber bundle. The length of the fiber bundle was 2 m, so that it was easily possible to connect the measuring head in the evaporator to the equipment (radiation source and detector, measuring amplifier, indicator) accomodated outside the apparatus, on a rack.

The spacing between lens 4 and the test glass in measuring position was 25 mm. Experience has shown that the measuring signal is independent of small variations of this spacing. It did not change even if the test glass 22 was not quite perpendicular to the optical axis of the measuring head, which may happen upon a not sufficiently careful insertion into the openings 21 of the turntable. For a relative measuring accuracy of 2%, deviations up to 1° from the vertical were tolerated.

The insensitiveness to disturbances is further increased if an as narrowbanded measuring beam as possible is used. For this purpose, a narrowband interference filter may be provided at any location of the path of rays, be it between the source of radiation and the fiber bundle, or in the beam within the measuring head, or between the exit fiber bundle and the detector.

In the present specification, the angle formed by the incident ray and the normal to the measuring surface is considered as the angle of incidence; thus, a perpendicular incidence of light on the measuring surface equals to a zero angle of incidence.

When an optical lens is mentioned in the specification, also a combined lens is to be understood by this term, thus a lens which is assembled of a plurality of individual lenses. The principal plane of the lens is defined herein as from where the distances $x$ and $y$ are to be measured, approximately coincides with the median plane of an individual lens. Its position may be determined more exactly while using well-known rules (which also applies to combined lenses).

I claim:

1. A device for measuring the reflection of a specularly reflecting surface comprising a radiation means and a radiation receiver, a converging lens having a focal length f interposed between said radiation means and a surface to be measured whereby a radiation beam from said radiation means is directed through said lens and onto the surface to be measured, said radiation means being located along the optical axis of said lens, and said radiation receiver including a receiving surface which circumscribes said radiation means for receiving the reflected beam from said surface whereby the distance between the principle plane of said lens and the surface to be measured is equal to:

$$(2X-f)(X-f)\cdot(f/2)$$

where X is the distance between the principle plane of said lens and radiation means.

2. A device for measuring the reflection of a specularly reflecting surface as defined in claim 1 wherein said receiving surface is disposed between said radiation means and said lens whereby said reflected beam passes through said lens and onto said receiving surface, and whereby said receiving surface is concentric with said radiation means so that the crosssectional area of the reflected beam falls completely within the receiving surface circumscribing the source of radiation.

3. A measuring device as defined in claim 2 wherein said radiation means and said radiation receiver comprises a first and second photoconductor respectively.

4. A measuring device as defined in claim 3 wherein the measuring radiation eminates from the end face of said first photoconductor and the end face of said second photoconductor defines said receiving surface.

5. A measuring device as defined in claim 4 wherein the end faces of said first and second photoconductors are coaxially disposed.

6. A measuring device as defined in claim 5 wherein each of said photoconductors comprise fiber bundles.

7. A measuring device as defined in claim 1 wherein said radiation means comprises the end face of a photoconductor.

8. A measuring device as defined in claim 1 wherein said radiation means comprises the image of a radiation source.

9. A measuring device as defined in claim 8 wherein said radiation receiver comprises a mirror having an aperture therein; said aperture being disposed in alignment with said optical axis and said mirror being obliquely inclined relative to said optical axis so that said radiation image is formed in plane intersecting said aperture whereby the measuring beam of radiation passes through said aperture and said lens onto said surface to be measured and the reflecting beam being returned through said lens and deflected by said mirror, and a focusing lens spaced from said mirror for focusing the reflected beam on a receiver.

10. A device for measuring the reflection of a specularly reflecting surface as defined in claim 1 and including a turntable for receiving test glass whereby said turntable is rotatably mounted relative to the optical axis for use in a vapor deposition apparatus.

11. A device for measuring the reflection of a specularly reflecting surface comprising a source of radiation, and a radiation detector means, a lens means having a focal length f interposed between said source of radiation and a surface to be measured whereby said source of radiation is disposed along the optical axis of the device, a second lens means interposed between said first mentioned lens means and said source of radiation to form a punctiform image of said radiation source at a distance X from said first mentioned lens means, a mirror having an aperture therein whereby said mirror is obliquely disposed relative to said optical axis with the aperture thereof at the point of said punctiform image so that the radiation beam of said image passes through said first mentioned lens means and onto said surface to be measured and the reflective beam being reflected from said surface back through said first mentioned lens means onto said mirror, said mirror defining the receiving surface for said reflected radiation beam, and a third lens means for focusing said reflected radiation beams onto said detector means whereby the first lens means is spaced from the surface to be measured a distance $$Y = (2X - f/X - f) \cdot (f/2).$$

* * * * *